United States Patent [19]

Vogt et al.

[11] Patent Number: 5,055,388
[45] Date of Patent: Oct. 8, 1991

[54] PROCESS AND REAGENT COMPOSITION FOR DETERMINATION OF FRUCTOSAMINE IN BODY FLUIDS

[75] Inventors: Bernd Vogt; Lieselotte Schellong, both of Tutzing; Joachim Siedel, Bernried; Joachim Ziegenhorn, Starnberg, all of Fed. Rep. of Germany

[73] Assignee: Boehringer Mannheim GmbH, Mannheim, Fed. Rep. of Germany

[21] Appl. No.: 190,600

[22] Filed: May 5, 1988

[30] Foreign Application Priority Data

May 14, 1987 [DE] Fed. Rep. of Germany ....... 3716218
Dec. 21, 1987 [DE] Fed. Rep. of Germany ....... 3743405

[51] Int. Cl.$^5$ .......................... C12Q 1/00; C12Q 1/60; C12Q 1/26; G01N 1/00
[52] U.S. Cl. .......................... 435/4; 435/10; 435/14; 435/25; 435/28; 435/269; 436/34; 436/63; 436/95; 436/174; 436/175; 436/904
[58] Field of Search .................. 435/4, 10, 25, 28, 14, 435/269; 436/95, 825, 66, 34, 63, 164, 174, 175

[56] References Cited

U.S. PATENT DOCUMENTS

| 4,282,001 | 8/1981 | Klose et al. | 23/230 B |
| 4,460,684 | 7/1984 | Bauer | 435/14 |
| 4,642,295 | 2/1987 | Baker | 436/87 |
| 4,645,742 | 2/1987 | Baker | 436/15 |
| 4,649,120 | 3/1987 | Steuer et al. | 436/13 |

FOREIGN PATENT DOCUMENTS 0085263 8/1983 European Pat. Off. .
0215170 3/1987 European Pat. Off. .
2910737 10/1980 Fed. Rep. of Germany .

OTHER PUBLICATIONS

Johnson et al., "Fructosamine: A New Approach to the Estimation of Serum...", Clin. Chim. Acta 127, 87–95 (1982).
Schleicher et al., "Specific Quantitation by HPLC of Protein (Lysine) Bound...", J. Clin. Chem. Clin. Biochem. 19, 81–7 (1981).

Primary Examiner—Ester L. Kepplinger
Assistant Examiner—Toni R. Scheiner
Attorney, Agent, or Firm—Felfe & Lynch

[57] ABSTRACT

A process for the determination of fructosamine in body fluids by the reaction of a sample solution with a color reagent, wherein the sample liquid is mixed with a buffer solution having a pH value of from 9 to 12, a color-forming reagent and uricase, as well as with at least one detergent, and the chronological change of the extinction is measured kinetically in a temperature range of from 20° to 40° C. at the earliest after 5 minutes.

25 Claims, 3 Drawing Sheets

PROCESS AND REAGENT COMPOSITION FOR DETERMINATION OF FRUCTOSAMINE IN BODY FLUIDS

BACKGROUND OF THE INVENTION

The present invention is concerned with a process for the determination of fructosamine in body fluids by the reaction of a sample solution with a colour reagent and with enzymes having an oxidising action, as well as with a reagent suitable therefor.

Fructosamines are formed in blood from glucose present therein. The carbonyl group of the glucose reacts with free protein amino residues causing the formation of Schiff's bases. By means of an Amadori rearrangement, there then arise the fructosamines which have a stable ketoamino bond. The half life time of the fructosamine is, because of the stability of this ketoamino bond, practically identical with that of the serum proteins, the half life time of which is, on average, about 21 days. Since the extent of the fructosamine formation is proportional to blood glucose level, the fructosamine content gives an indication of sugar metabolism. The sugar metabolism must be continuously monitored, for example, in the case of diabetics. Since the blood glucose level is subject to considerable variation, its determination provides the physician with the metabolic position only at the time of sampling the blood. A further possibility for testing for sugar metabolism consists in the determination of the glycosilated haemoglobin ($HbA_1$), this determination being suitable for a long-term monitoring of the sugar metabolism. However, in order now to have a medium term control, the measurement of the fructosamine content is very suitable since its half life time permits the metabolic control of diabetics by dieting and therapeutic measures over an average period of time of about 3 weeks. In combination with known clinical-diagnostic parameters, blood glucose, as well as glycosilated haemoglobin, by means of a serum fructosamine determination, there can now be provided a further dependable, specific and practical method for monitoring diabetics.

The hitherto known processes for the determination of fructosamine (for example Johnson et al., *Clin. Chim. Acta,* 127, 87-95/1982) depend upon the fact that fructosamine, which in an aqueous alkaline medium is present in the enol form and can easily be oxidised in this form, is reacted with an oxidation agent (colour-producing compound) which, in reduced form, is coloured, for example a tetrazolium salt. The formazan coloured material thereby formed can then be measured photometrically and is proportional to the amount of fructosamine.

However, this test principle has the disadvantage that, besides fructosamine, all easily oxidisable components present in the sample material, for example uric acid and bilirubin, or medicaments, for example α-methyldopa, as well as ascorbic acid, give rise to false measurement results since they also reduce the colour-providing compounds and cause formation of additional coloured material.

Furthermore, the known fructosamine determination processes are disturbed by the total amount of the protein content, which varies from sample to sample. This results in measurement value variations and thereby reduces the sensitivity of the determination process.

These disturbances are known as matrix effects and appear particularly when additional proteins are added, such as is usually the case in the preparation of standard solutions. Thus, for example, increasing amounts of protein slow down the colour reaction with desoxymorpholinofructose (DMF) which is frequently added as fructosamine analogue in such standard solutions for calibration purposes.

Finally, a comparison with an HPLC reference method (see E. Schleicher et al., *J. Clin. Chem. Clin. Biochem.,* 19, 81-87/1981) has shown that, with the known processes, there is obtained a high colour signal axis intercept, which corresponds to about 50% of the signal of an average, normal serum collective.

Further difficulties arise in the case of fructosamine determinations in hyperlipidaemic sera. In general, in order to be able to obtain a sufficiently large measurement signal even in the case of low fructosamine concentrations in a sample, it is necessary to use a ratio of sample to reagent of 0.1. In the case of excessive triglyceride concentrations, however, where there is a high proportion of sample material, the resulting turbidity of the test batch has a negative effect in the case of a photometric measurement. The fructosamine determination is then made considerably more difficult or even prevented.

In European Patent Specification No. 0215170, there is described a fructosamine determination using tetrazolium salts at pH 10 to 14 as an end point determination. Disturbances by ascorbic acid and glutathione are thereby overcome by the addition of strong bases, oxidation agents or enzymes, or by salting out. However, in this way, the disturbances due to lipaemic, icteric and uric acid-rich sera cannot be overcome. Furthermore, the carrying out of the test according to European Patent Specification No. 0215170 requires a time-consuming pre-reaction which cannot be integrated into most automatic anaylsers.

One of these difficulties was solved by a two-step process in which, in a first step, a neutral to acidic pH value is adjusted in the sample solution at which the fructosamine is present in the keto form and, therefore, practically cannot be oxidised. At this pH value, oxidising-acting enzymes are then added until the non-specifically reducing sample components have reacted away. The pH value is then increased into the alkaline range, whereby the fructosamine again passes over into its enol form and then the tetrazolium salt is added thereto which reacts with the fructosamine. In this way, the exactitude and the sensitivity of the known fructosamine processes could be very considerably improved.

It is an object of the present invention to provide a process which can be carried out in one step and permits a determination of fructosamine in body fluids which is at least as accurate and sensitive as that already achieved for the two-step process.

SUMMARY OF THE INVENTION

Thus, according to the present invention, there is provided a process for the determination of fructosamine in body fluids by the reaction of a sample solution with a colour reagent, wherein the sample liquid is mixed with a buffer solution having a pH value of from 9 to 12, a colour-forming compound and uricase, as well as with at least one detergent, and the chronological change of the extinction is measured kinetically in a temperature range of from 20° to 40° C. at the earliest after 5 minutes.

Surprisingly, we have ascertained that, in the case of the addition of the colour-forming compound, uricase and detergent to a sample solution at a pH value of from 9 to 12, the disturbing oxidisable compounds react away quickly and turbidities are rapidly clarified so that, after a short pre-incubation time, only the fructosamine reacts specifically with the colour-forming compound. In this way, it is possible to determine the fructosamine in a one-step process with greater exactitude than was possible with the previously known processes.

Figure 1:
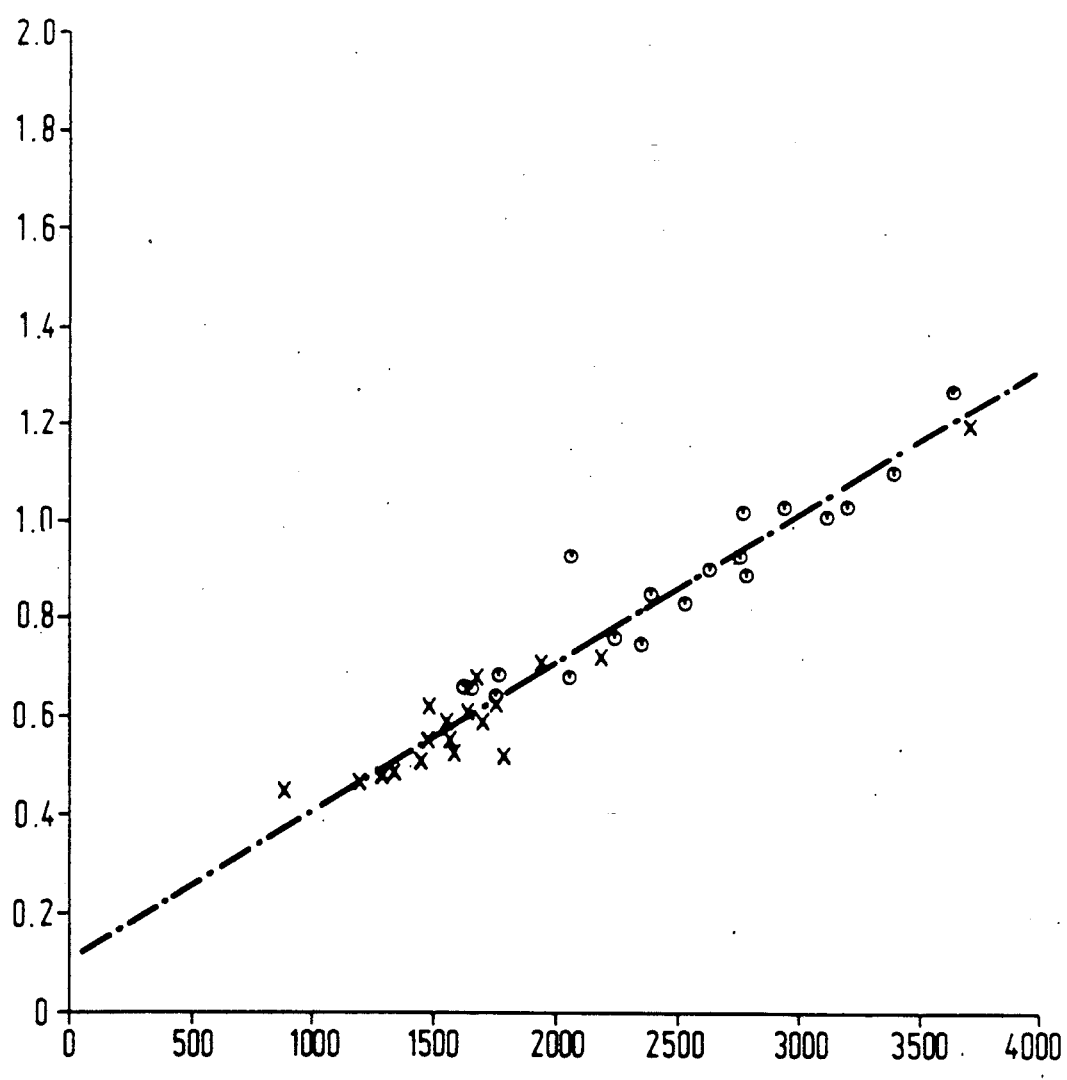
FIG. 1 is a comparison of the automated process of this invention with the HPLC method.

In all these figures the circle symbols represent sera of diabetics and the X symbols represent normal sera.

DETAILED DISCLOSURE

For the determination of the fructosamine, the sample liquid is adjusted with a buffer solution to a pH value of from 9 to 12. At this alkaline pH value, the fructosamine is then present in its enol form. The pH value is preferably kept in a range of from 10 to 11. For the preparation of the buffer solution, all substances can be used which themselves do not act reducingly and the buffer action of which lies approximately in the desired range. It is especially preferred to use a carbonate buffer, the concentration of which preferably lies in the range of from 50 to 500 mMole/liter.

Uricase is added in order to allow disturbing sample components to react away. The main disturbing substances, for example uric acid, are oxidised with this enzyme and cannot disturb the determination. The concentration of the uricase therefore depends upon the concentration of the disturbing substances to be removed. These concentrations are usually in a range of from 1 to 15 U/ml. Thus, for example, the uricase is preferably used in a concentration of from 2 to 10 U/ml.

A peroxidatively-active enzyme is preferably added. In this way, there can be achieved a further improvement, especially with regard to the correlation of the HPLC reference method. The peroxidately-active enzyme is preferably present in a concentration of from 1 to 5 U/ml.

As peroxidately-active enzymes, there can be used compounds which act oxidizingly with the consumption of hydrogen peroxide, for example peroxidase (EC 1.11.1.7) or microperoxidases (haemin-containing low molecular weight cleavage products of peroxidase). It is preferred to use peroxidase, especially from horseradish. It is especially preferred to use a water-soluble polymer-bound peroxidase, such as is described in Federal Republic of Germany Patent Specification No. 3541186.4.

As further component, at least one detergent is added to the sample liquid. Detergents serve, in the first place, to remove sample components which give rise to turbidities. Furthermore, they surprisingly also eliminate the influence of the protein matrix and thus improve the linearity of the relationship between measurement signal and concentration of the sample protein. For this purpose, a large range of detergents is available, all of which can be used. As detergent, it is preferred to use a non-ionic, anionic and/or zwitterionic detergent, a mixture of a non-ionic and anionic detergent being especially preferred. As non-ionic detergent, there is preferably used a straight-chained or branched alkanol-polyglycol ether with about 8 to 12 carbon atoms in the alkanol part and on average 4 to 8 glycol units per molecule. A preferred anionic detergent is an alkali metal salt of a bile acid, sodium cholate being especially preferably used. A preferred zwitterionic detergent is a bile acid derivative, for example 3-((3-cholamidopropyl)-dimethylammonio)-1-propane-sulphonate (CHAPS). Furthermore, it is especially preferred also to add a cationic detergent so that several different detergents are present in the sample solution. As cationic detergents, there are preferably used quaternary ammonium compounds or quaternary pyridinium compounds or mixtures of these two classes of substances. The concentration of the detergents can be varied within a wide range. Concentrations in the range of from 0.5 to 10% by weight, referred to the content of pure substance, have proved to be suitable. The non-ionic detergent is especially preferably used in a concentration of from 1 to 5% by weight. The anionic or zwitterionic detergent is especially preferably used in a range of from 4 to 10 mMole/liter. The cationic detergent can be used preferably in a concentration of up to 5% by weight.

As colour-forming compounds, there can be used compounds which act oxidisingly on fructosamine and thereby change their colour, for example tetrazolium salt compounds. Tetrazolium salts are known in analytical chemistry and are frequently used. They are derivatives of 1,2,3,4-tetrazole and have a quaternary nitrogen atom. Tetrazolium salts are easily reduced and, with the addition of hydrogen, form strongly coloured formazans which can be very well determined photometrically. There are a number of tetrazolium salts which can be used for the process according to the present invention, examples of which include 3-(4,5-dimethylthiazolyl-2)-2,4-diphenyltetrazolium bromide (MTT), 2-(p-iodophenyl)-3-(p-nitrophenyl)-5-phenyltetrazolium chloride (INT), 2,2',5,5'-tetra-(p-nitrophenyl)-3,3'-(3,3'-dimethoxy-4,4'-diphenylene)-ditetrazolium chloride (TNBT), 2,2'-di-(p-nitrophenyl)-5,5'-diphenyl-3,3'-(3,3'-dimethoxy-4,4'-diphenylene)-ditetrazolium chloride (NBT), 2,2'-p-diphenylene-3,3',5,5'-tetraphenyl-ditetrazolium chloride (neotetrazolium chloride) (NT), 2,3,5-triphenyltetrazolium chloride (TT). Nitrotetrazolium blue (NBT) is also especially preferred as tetrazolium salt.

The colour-forming compounds are preferably used in a concentration of from 0.1 to 1 mMole/liter and especially preferably of from 0.2 to 0.6 mMole/liter.

For the determination of fructosamine in a sample liquid, all the components are added in one step. The reaction takes place at a temperature in the range of from about 20° to 40° C., the incubation preferably being carried out at a temperature in the range of from 25° to 37° C.

For the determination of the fructosamine, the reaction is monitored photometrically. Immediately after the addition of all of the components, low molecular weight serum components react away very quickly and this results in a steep rise of the extinction curve. After the reacting away of the disturbing substances, only the fructosamine still reacts and the extinction curve flattens out somewhat. The kinetic measurement should then take place in this range, this being the case about 5 to 15 minutes after the addition of the reagents. In this time interval, at least 2 measurements are then carried out. The time differences between the measurements are variable and they can be chosen depending upon the apparatus used. The time difference can be in the region of a few seconds but can also be in the region of a few minutes.

In some cases, it is preferable to compare the measurement values obtained with those of a standard solution. Appropriate standard solutions are known. For example, for this purpose, there can be used the standard described by Johnson et al. in Clin. Chim. Acta. 127, 87-95/1982 which is based on a matrix of human albumin with definite additions of a synthetic fructosamine. As synthetic fructosamine, there is used 1-desoxy-1-morpholinofructose (DMF). The determined serum fructosamine concentration in the sample is, in the case of the use of this standard, given in DMF equivalents.

Surprisingly, with the process according to the present invention, it is also possible considerably to reduce the ratio of sample to reagent volume from 0.1, which is usual according to the process of Johnson et al. without, in the case of the same measurement interval and incubation at the same temperature, the measurement signal with a definite amount of fructosamine analogue employed as sample becoming significantly smaller in comparison with the method described by Johnson et al. At the same time, the protein matrix influence is linearised. In addition, there is observed practically no axis intercept in the case of a comparison with the already-mentioned HPLC reference method.

The process according to the present invention for the determination of fructosamine in body fluids can be carried out not only in solution but also on a dry chemical test carrier. The components used according to the present invention are applied in known manner to solid carriers. Appropriate solid carriers, as well as processes for the application of these materials or material mixtures to such carriers, are known to the expert. As carrier materials, there can be used, for example, absorbent materials, such as paper and fleece. The materials to be applied can be taken up in one or more impregnation solutions. With these solutions, the carrier is impregnated or sprayed and subsequently dried. Another variant is to introduce the components used according to the present invention into reagent films. For this purpose, the substances or substance mixtures are worked up, for example, according to the processes described in Federal Republic of Germany Patent Specifications Nos. 1598153 or 2910134 to give reagent films.

The present invention also provides a reagent mixture for the determination of fructosamine in body fluids containing a colour reagent, which contains a buffer substance with a pH value of from 9 to 12, a colour-forming compound, uricase and at least one detergent. The reagent mixture can be present in solution but it can also be present in known manner in dry form to be impregnated on a carrier. A peroxidate-active enzyme is preferably also added. As colour-forming compound, it is preferred to use a tetrazolium salt.

The present invention enables fructosamine to be determined in a simple manner very precisely and specifically. Surprisingly, this takes place by means of a combination of several components.

Figure 2:
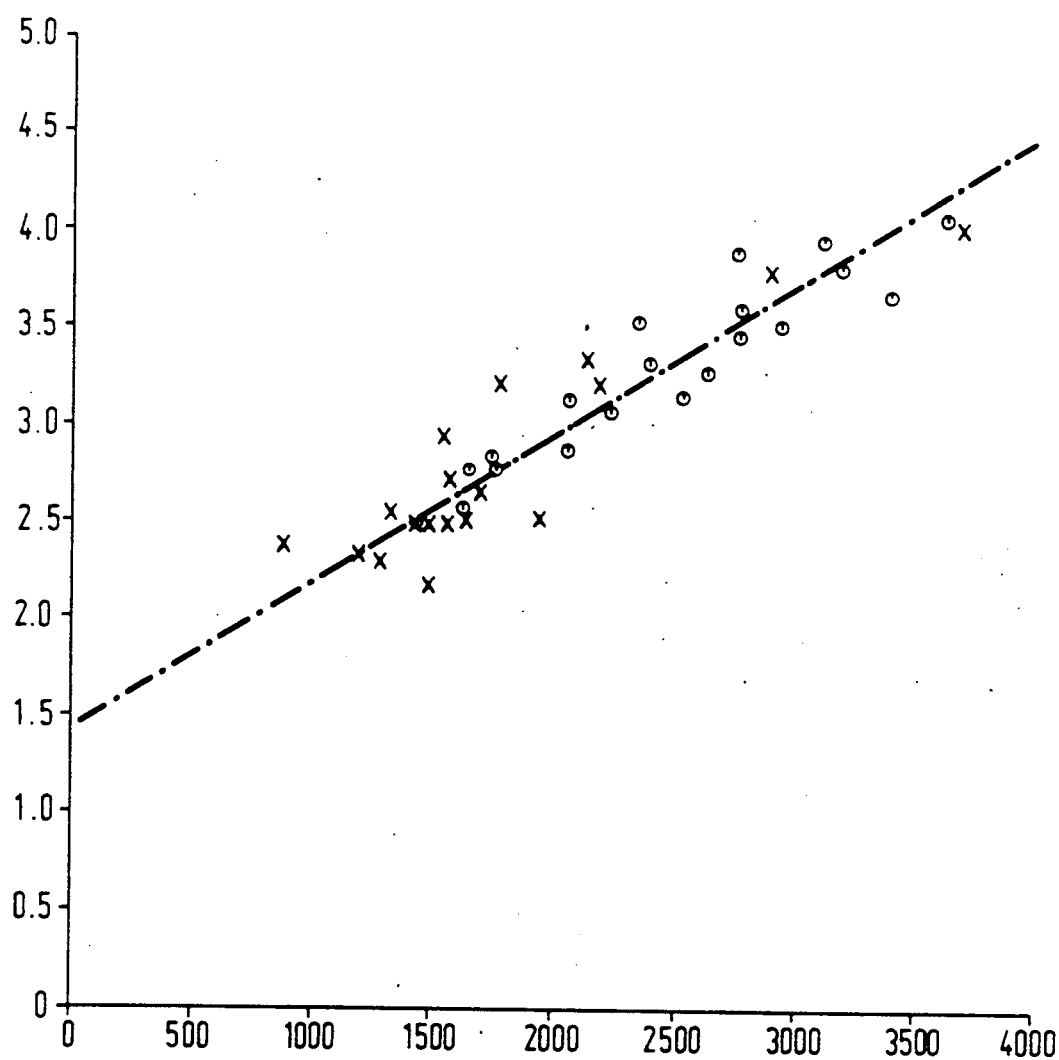
FIG. 2 is a comparison of the Johnson process with the HPLC method.
Figure 3:
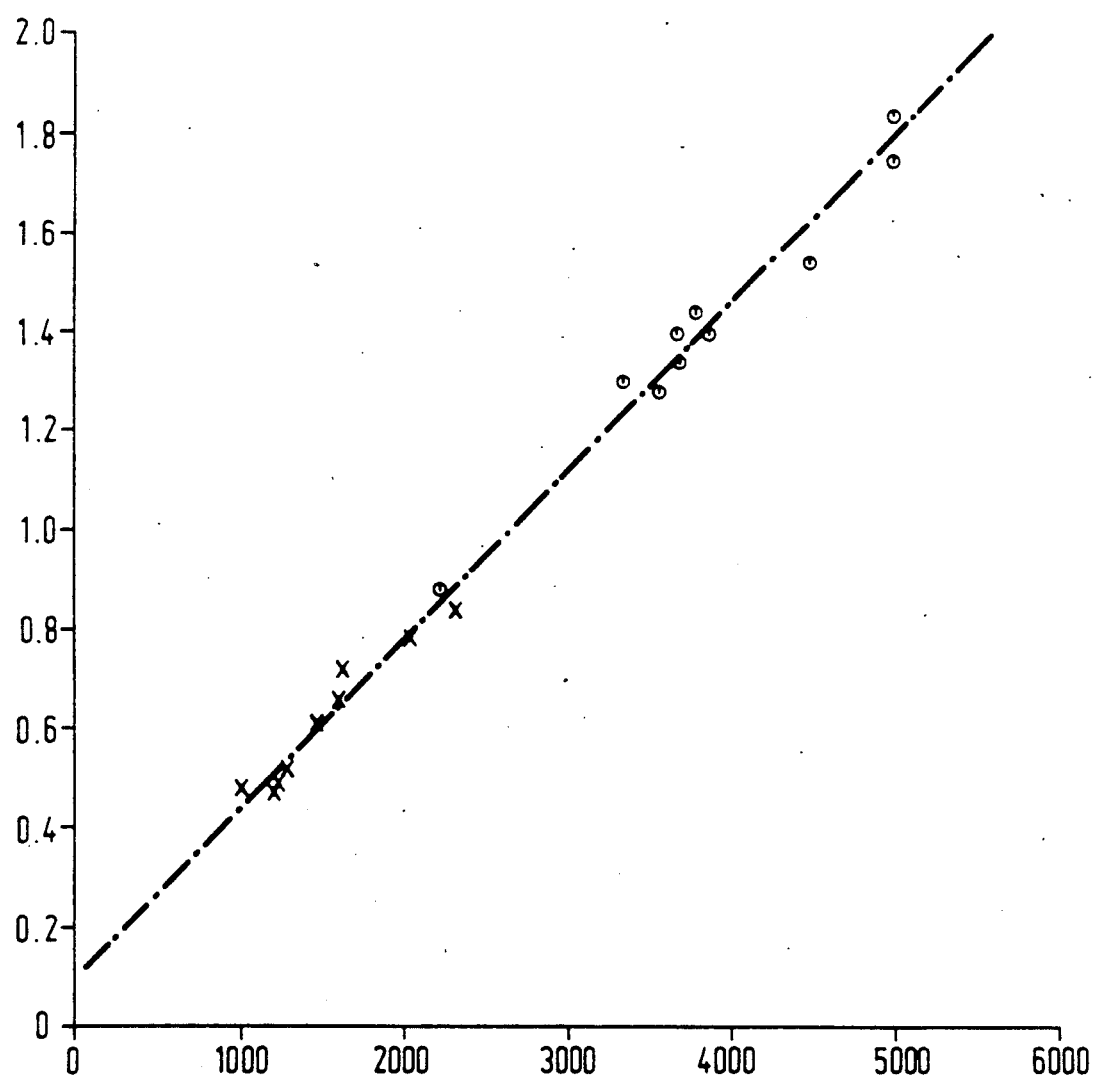
FIG. 3 is a comparison of the process of this invention manually performed with the HPLC method.

The present invention will now be explained in more detail in the following Examples, with reference to the accompanying drawings, in which:

FIG. 1 is a comparison of the process according to the present invention employing an automatic analyser with the HPLC reference method; there are plotted the fructosamine concentrations of patient sera determined by the process according to the present invention against the relative units which are obtained with the HPLC method (correlation coefficient: 0.965);

FIG. 2—comparison of the process according to Johnson et al. with the HPLC method (correlation coefficient: 0.933); and FIG. 3—comparison of the process according to the present invention manually performed with the HPLC method (correlation coefficient: 0.995).

EXAMPLE 1

Determination of Fructosamine in Serum by the Process According to the Present Invention on an Automatic Analyser.

Reagent Composition 200 mMole/liter sodium carbonate buffer (pH 10.35), 1.2% by weight non-ionic detergent (Lutensol ON 60), 3.5 mMole/liter sodium cholate, 4 U/ml. uricase, 2 U/ml. peroxidase and 0.5 mMole/liter nitrotetrazolium blue (NBT).

Method of Determination

7 $\mu$l. of sample are added to 350 $\mu$l. of reagent and the extinction is determined at 37° C. on a Hitachi 704 automatic analyser at $\lambda = 546/700$ nm. The kinetics were evaluated between the 8th and 10th minute after the addition of the reagent.

The results were plotted against the measurement values which were obtained with the HPLC reference method (see J. Clin. Chem. Clin. Biochem., 19, 81-87/1981). As HPLC measurement values, there were, in each case, used relative peak surface units. FIG. 1 of the accompanying drawings shows the results obtained.

The HPLC method was also used as reference method in the following Examples.

EXAMPLE 2

Determination of Fructosamine in Serum by the Method of Johnson et al. on an Automatic Analyser Reagent Composition 0.1 mole/liter sodium carbonate buffer (pH 10.35) and 0.25 mMole/liter nitrotetrazolium blue.

Method of Determination

20 $\mu$l. of sample were mixed with 200 $\mu$l. of reagent and 50 $\mu$l. of water (diluent) and the extinction was determined chronologically at 37° C. on a Cobas Bio ® automatic analyser (Hoffmann LaRoche) at $\lambda = 530$ nm. For the determination of the fructosamine concentration, the kinetics were evaluated between the 10th and 15th minute after addition of the reagent. The results obtained are illustrated in FIG. 2 of the accompanying drawings.

A comparison of the results of Examples 1 and 2 shows that, with the process according to the present invention, in comparison with the prior art, there is obtained an improvement of the correlation of the measurement values and a substantial reduction of axis intercept in comparison with the HPLC reference method.

EXAMPLE 3

Determination of Fructosamine in Serum by the Process According to the Present Invention Manually Performed Reagent Composition The composition of the reagent is analogous to that given in Example 1.

Method of Determination 1 ml. of reagent is added to 20 μl. of sample at 37° C. and the kinetics evaluated in the range between the 10th and 15th minute after addition of the sample, measured at 546 nm.

If the measurement is carried out at ambient temperature, then because of the lower reactivity, the evaluation must be carried out over a longer period of time (between the 10th and 30th minute), the results obtained being analogous (see FIG. 3 of the accompanying drawings).

EXAMPLE 4

This Example compares the disturbance of the fructosamine determination by lipaemic sera, bilirubin and uric acid between the process according to the present invention and the process according to Johnson et al.

The reagents and process conditions described in Examples 1 and 2 are used.

The effects of the various disturbing factors on both methods are shown in the following Table I, there being given the average deviation from the regression lines according to FIGS. 1 and 2 of the accompanying drawings. It is thereby shown that the influence of all disturbing factors in the case of the process according to the present invention is smaller than according to the prior art.

TABLE I

| | average deviation from the regression lines | |
|---|---|---|
| disturbance | Example 1 (according to the present invention) | Example 2 (according to Johnson et al.) |
| lipaemic sera (n = 8) average triglyceride content 1440 mg./dl. (600–2280 mg./dl.) | +7% | −25% |
| icteric sera (n = 9) average bilirubin content 16.7 mg./dl. (8.2–32 mg./dl.) | +22% | +46% |
| uric acid sera (n = 10) average uric acid content 9.5 mg./dl. (8.2–13.4 mg./dl.) | −2% | −7% |

EXAMPLE 5

Elimination of the Protein Matrix Influence by the Addition of Detergent

The process is analogous to Example 1. As "reagent without detergent" there is used a reagent corresponding to Example 1 which does not contain sodium cholate and Lutensol. As sample, there is used desoxymorpholinofructose (DMF) in a concentration of 2.5 mMole/liter. As protein, there is used bovine serum albumin (BSA). The following Table II shows the results obtained.

TABLE II

| | DMF signal (mE/min.) | |
|---|---|---|
| protein matrix g./dl. BSA | reagent according to Example 1 | reagent without detergent |
| 2 | 16 | 12 |
| 4 | 15 | 11 |
| 6 | 16 | 10 |
| 8 | 15 | 9 |
| 10 | 15 | 8 |

The DMF signal (extinction) is obtained from the difference of the measurement value for DMF−BSA from which the measurement value for BSA alone is subtracted.

It can be seen that the DMF signal, in the case of the use of a reagent according to Example 1, is independent of the protein matrix, whereas in the case of the otherwise identical reagent but without the addition of detergent, it decreases with increasing protein content.

We claim:

1. A process for the determination of fructosamine in body fluids by the reaction of a sample solution with a colour-forming reagent comprising simultaneously mixing a sample liquid with a (i) a buffer solution having a pH of from 9 to 12, (ii) a tetrazolium salt as the colour-forming reagent, (iii) uricase in an amount sufficient to eliminate uric acid interference and (iv) at least one detergent in an amount sufficient to reduce turbidity in said sample liquid, and measuring chronological change of extinction over a period of time no earlier than 5 minutes after mixing, at a temperature range of from 20°–40° C.

2. A process according to claim 1, wherein a peroxidatively-active enzyme is added.

3. A process according to claim 1 wherein the buffer solution has a pH value of from 10 to 11.

4. A process according to claim 3, in which the buffer is sodium or potassium carbonate.

5. A process according to claim 1 wherein the buffer is used in a concentration of from 50 to 500 mMole/liter.

6. A process according to claim 1, wherein the detergent is selected from the group consisting of non-ionic detergents anionic detergents, zwitterrionic detergents and mixture thereof.

7. A process according to claim 6, wherein the non-ionic detergent is a straight-chained or branched alkanol-polyglycol ether with 8 to 12 carbon atoms in the alkanol part and with, on average, 4 to 8 glycol units per molecule.

8. A process according to claim 7, wherein the alkanol-polyglycol ether is used in a concentration of from 1 to 5% by weight.

9. A process according to claim 6, wherein the anionic detergent is an alkali metal salt of a bile acid.

10. A process according to claim 9, wherein the alkali metal salt of a bile acid is sodium cholate.

11. A process according to claim 6, wherein the anionic detergent is used in a concentration of from 1 to 10 mMole/liter.

12. A process according to claim 6, wherein a cationic detergent is additionally used.

13. A process according to claim 12, wherein the cationic detergent is selected from the group consisting of quaternary ammonium compounds, pyridinium compounds and mixtures thereof.

14. A process according to claim 1, wherein uricase is used in a concentration of from 2 to 10 U/ml.

15. A process according to claim 2, wherein the peroxidatively-active enzyme is used in a concentration of from 1 to 5 U/ml.

16. A process according to claim 15, wherein peroxidase is used as the peroxidatively-active enzyme.

17. A process according to claim 1, wherein the tetrazolium salt is used in a concentration of from 0.1 to 1 mMole/liter.

18. A process according to claim 17, wherein the tetrazolium salt is used in a concentration of from 0.2 to 0.6 mMole/liter.

19. A process according to claim 1, wherein nitrotetrazolium blue is used as the tetrazolium salt 20. A process according to claim 1, wherein said measuring takes place 5 to 15 minutes after mixing.

21. A process according to claim 1, wherein said measuring takes place at a temperature of from 25° to 37° C.

22. A process according to claim 1, wherein the buffer solution has a pH value of from 10 to 11 and is used in a concentration of from 50 to 500 mMoles per liter, the uricase is used in a concentration of from 2 to 10 U/ml, the detergent comprises (1) a nonionic and anionic detergent and (2) a cationic detergent, and said measuring takes place 5 to 15 minutes after mixing at a temperature of from 25° to 37° C.

23. A process according to claim 22, wherein sodium or potassium carbonate is used as the buffer, the nonionic detergent is a straight-chained or banched alkanolpolyglycol ether with 8 to 12 carbon atoms in the alkanol group and with, on average, 4 to 8 glycol units per molecule and is used in a concentration of from 1 to 5% by weight, the anionic detergent is sodium cholate used in concentration of from 1 to 10 mMoles per liter, the cationic detergent is a quarternary ammonium or pyridinium compound or a mixture thereof, and the tetrazolium salt is nitrotetrazolium blue used in a concentration of from 0.1 to 1 mMole per liter.

24. A process according to claim 22, wherein a peroxidatively-active enzyme in a concentration of from 1 to 5 U/ml. is added.

25. A process according to claim 24, wherein peroxidase is used as the peroxidatively-active enzyme.

* * * * *